United States Patent [19]

Knight et al.

[11] Patent Number: 4,910,132

[45] Date of Patent: Mar. 20, 1990

[54] VIRUS-FREE IN VITRO ASSAY FOR ANTI-HIV AGENTS

[75] Inventors: David M. Knight, Paoli; John Ghrayeb, Thorndale, both of Pa.

[73] Assignee: Centocor, Malvern, Pa.

[21] Appl. No.: 49,051

[22] Filed: May 12, 1987

[51] Int. Cl.[4] .................... G01N 33/569; C12N 15/00
[52] U.S. Cl. .......................................... 435/5; 435/29; 435/33; 435/34; 435/172.3; 435/320; 436/63; 935/76; 935/27; 935/29; 935/70
[58] Field of Search ................ 435/5, 29, 33, 34, 320, 435/172.3; 436/63; 935/27, 76, 29, 70

[56] References Cited

U.S. PATENT DOCUMENTS 4,704,357 11/1987 Mitsuya et al. ..................... 435/29

OTHER PUBLICATIONS

Mitsuya et al., "Rapid in Vitro Systems for Assessing Activity of Agents Against HTLV-III/LAV" in AIDS: Modern Concepts and Therapeutic Challenges, S. Broder, ed., Marcel Dekker Inc., N.Y., 1987, pp. 303–333.

Sodroski et al., "A Second Post–Transcriptional *trans*-Activator Gene Required for HTLV–III Replication", Nature, 321 (1986) 412–417.

Feinberg et al., "HTLV-III Expression and Production Involve Complex Regulation at the Levels of Splicing and Translation of Viral RNA", Cell, 46 (1986) 807–817.

Fisher et al., "The *trans*-Activator Gene of HTLV-III is Essential for Virus Replication", Nature, 320 (1986) 367–371.

Dayton et al., "The *Trans*-Activator Gene of the Human T Cell Lymphotropic Virus Type III is Required for Replication", Cell, 44 (1986) 941–947.

Meusing et al., "Regulation of mRNA Accumulation by a Human Immunodeficiency Virus *Trans*-Activator Protein", Cell, 48 (1987) 691–701.

Knight et al., "Expression of the Art/Trs Protein of HIV and Study of Its Role in Viral Envelope Synthesis", Science, 236 (1987) 837–840.

Goh et al., Identification of a Protein Encoded by the *trans* Activator Gene *tat*III of Human T-Cell Lymphotropic Retrovirus Type III, J. Virol, 59 (1986) 181–184.

*Primary Examiner*—Christine M. Nucker
*Attorney, Agent, or Firm*—Sughrue, Mion, Zinn, Macpeak & Seas

[57] ABSTRACT

A virus-free assay to identify agents that interfere with the life cycle of HIV which comprises: (1) expressing in mammalian cells in the presence or absence of one or more of said agents, HIV gp120, the gene product of HIV tat, the gene product of HIV art/trs, all under the control of an HIV LTR promoter, and a control protein, not under the control of the HIV LTR promoter, such that infectious HIV particles are not produced; (2) quantitating the amount of the gp120 produced relative to the amount of control protein produced; and (3) comparing the relative amount of the gp120 produced in the presence of said one or more agents to the relative amount of the gp120 produced in the absence of said one or more agents. A plasmid capable of expressing the gene product of HIV art/trs in mammalian cells such that infectious HIV particles are not produced, which includes: (1) a DNA fragment comprising an HIV LTR promoter, and (2) and HIV cDNA restriction fragment carrying the art/trs gene but not the ATG start codon of the first coding exon for tat.

10 Claims, 5 Drawing Sheets

FIG. IA
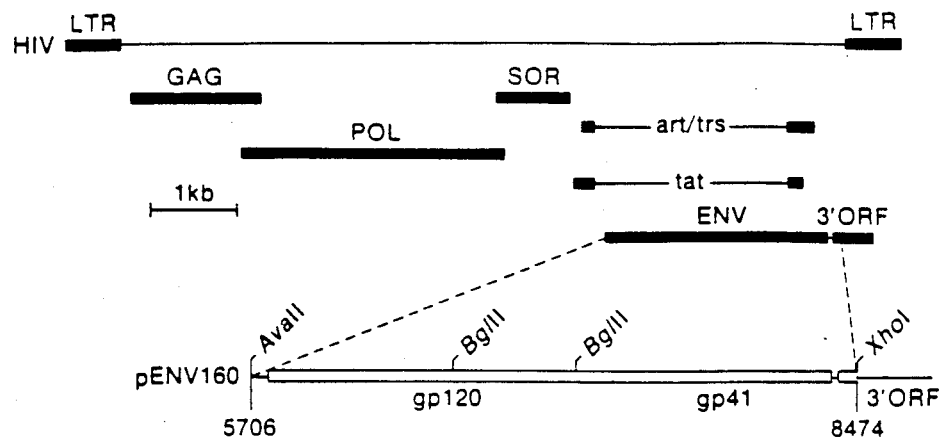

VIRUS-FREE IN VITRO ASSAY FOR ANTI-HIV AGENTS

FIELD OF THE INVENTION

The present invention relates to an assay for identifying agents that interfere with the life cycle of infectious Human Immunodeficiency Virus, the cause of Acquired Immunodeficiency Syndrome. The assay can be performed without producing infectious virus particles. The present invention also relates to a novel plasmid capable of expressing the gene product of the Human Immunodeficiency Virus art/trs region which is useful in the assay.

BACKGROUND OF THE INVENTION

Human Immunodeficiency Virus (HIV, HTLV-III, LAV, ARV), the cause of Acquired Immunodeficiency Syndrome (AIDS) and Aids Related Complex (ARC), differs from most known retroviruses in the complexity of its genetic organization. (For simplicity, Human Immunodeficiency Virus will hereinafter be designated as HIV. but it is understood to include all other designations which have been used in the literature to identify the virus which causes ARC and AIDS.) In addition to the Long Terminal Repeats (LTRs) and the gag, pol, and env genes present in all retroviruses, HIV has several genes which contribute to a system of genetic regulation far more complex than most retroviruses. Among these are two genes, tat and art/trs, that are both required for viral replication in vitro (A. I. Dayton et al., Cell 44, 941 (1986); A. G. Fisher et al., Nature 320, 367 (1986); and J. Sodroski et al., Nature 321, 412 (1986)). Further, the tat gene is known to code for a "transactivator" that stimulates expression of other HIV genes and the art/trs gene is believed to code for another transactivator.

Hereinafter, the genes are designated by underlining (e.g., tat and art/trs) and the gene products are designated with no underlining (e.g., tat and art/trs).

The tat gene product has been identified as a 14 kDa protein (W. C. Goh et al., J. Virology 59, 181 (1986) and M. B. Feinberg et al., Cell 46, 807 (1986)) but the putative art/trs gene product has not previously been identified.

One important viral gene regulated by tat and art/trs is the env gene which encodes the envelope glycoproteins gp120 and gp41. As a component of the viral envelope, gp120 is crucial to the interaction of the virus with its cellular receptor (J. S. McDougal et al., Science 231, 382 (1986) and P. J. Maddon et al., Cell 47, 333 (1986)) and may also contribute to the cytopathogenicity of HIV through its involvement in syncytium formation (J. Sodroski et al., Nature 322, 470 (1986). It has been reported that the degree of cytopathic effect of the virus directly correlates with the amount of viral envelope protein synthesized by an infected cell (M. B. Feinberg et al., supra).

The mechanisms by which tat and art/trs regulate env gene expression are not clearly understood. Both tat and the putative art/trs appear to act, at least in part, post-transcriptionally. In tat or art/trs defective proviral mutants there appears to be substantial viral RNA produced after proviral transfection although viral protein levels are greatly reduced (J. Sodroski et al., Nature 321, supra): M. B. Feinberg et al., supra; and C. A. Rosen et al., Nature 319, 941 (1986)) suggesting the involvement of translational control. The tat gene product may also increase the steady-state level of mRNA transcribed from the LTR although there is not yet a consensus on this point (for review see I. S. Y. Chen, Cell 47, 1 (1986)).

It has been difficult to assign precise roles to the tat and art/trs proteins in part because the two genes coding therefore overlap (in different reading frames) with each other and with the envelope gene. Studies utilizing tat or art/trs proviral deletions have been difficult to interpret due to the possibility of more than one functional unit being altered simultaneously, and the potential for other viral genes influencing the results. Further, studies that examine the effects of tat or art/trs upon the HIV LTR-directed synthesis of heterologous gene products may not be valid models if translational regulation that relies upon mRNA structure is involved.

One important aspect of research involving HIV is the development of assays to identify agents that have potential for treating AIDS victims. Such assays are designed to screen for agents that selectively interfere with the production of infectious HIV. To date, however, all such known assays are cumbersome, time consuming and require elaborate safety precautions because the assays result in the production of infectious virus. Examples of known assay systems are described in C. P. Schaffner et al., Biochem. Pharmacol. 35, 4110-4113 (1986), P. Sarin et al., N. Engl. J. Med. 313, 1289-1290 (1985), E. Terwilliger et al., J. Virol. 60, 754-760 (1986); J. Balzarini et al., Int. J. Cancer 37, 451 (1986); and H. Mitsuya and S. Broder, P.N.A.S. U.S.A. 83, 1911 (March 1986).

Two such assays look at the in vitro inhibitory effects of suramin and other various compounds which appear to inhibit activity of viral reverse transcriptase on the infectivity and replication of HIV in two test systems. J. Balzarini et al., supra. One of these assays involves following the cytopathic effect of HIV on ATH8 cells, a T-cell clone with high susceptibility to HIV, and the other of these assays involves following the expression of HIV p24 gag protein in H9 cells infected with HIV.

The ATH8 test system requires infecting the cells with HIV, culturing the infected cells in culture medium in the presence of test compound, incubating for a week or more, and then at 7-8 days after virus infection counting the number of viable cells and comparing to controls.

The H9 test system requires infecting the cells with HIV, culturing the infected cells in culture medium in the presence of test compound, incubating for a week or more, and then at days 9, 10, and 11 after virus infection determining the percentage of cells expressing the HIV p24 gag protein.

The capacity of purine and pyrimidine nucleoside derivatives to inhibit the infectivity and cytopathic effect of HIV in vitro using test systems similar to those described above has also been examined. H. Mitsuya and S. Broder, supra.

Not only are the above assays time consuming but all involve the use and expression of infectious HIV.

In view of the above, the advantages of an in vitro assay system which is relatively rapid and which does not give rise to infectious HIV are apparent.

However, the development of such an assay system has been hampered in part due to the complexity of the genetic organization of HIV as described above and also due to the fact that the putative art/trs gene product has not previously been identified.

SUMMARY OF THE INVENTION

Accordingly, one object of the present invention is to provide a virus-free in vitro assay to identify anti-HIV agents.

Another object of the present invention is to provide a virus-free in vitro assay to identify anti-HIV agents that provides a large number of possible targets for inhibition by the anti-HIV agents.

A further object of the present invention is to provide a virus-free in vitro assay to identify anti-HIV agents wherein the targets of the agents are virus-specific and have no known cellular homologs, and, as a result, any anti-HIV agents detected would probably not be very toxic (if at all) to human cells thereby providing a clinical advantage during therapy.

An even further object of the present invention is to provide an assay for screening anti-HIV agents which is less-time consuming than current screening assays and requires only several days rather than several weeks to perform.

A still further object of the present invention is to provide an assay for screening anti-HIV agents which does not require elaborate safety precautions because no infectious HIV virus is involved.

A still further object of the present invention is to provide an assay for detecting anti-HIV agents which has the potential to detect new classes of anti-HIV agents which may interfere with crucial events in the viral life cycle.

These and other objects have been attained by providing a virus-free assay to identify agents that interfere with the life cycle of HIV which comprises: (1) expressing in mammalian cells in the presence or absence of one or more of the agents, HIV gp120, the gene product of HIV tat, the gene product of HIV art/trs, all under the control of an HIV LTR promoter, and a control protein, not under the control of the HIV LTR promoter, such that infectious HIV particles are not produced; (2) quantitating the amount of the gp120 produced relative to the amount of the control protein produced; and (3) comparing the relative amount of the gp120 produced in the presence of said one or more agents to the relative amount of the gp120 produced in the absence of said one or more agents.

In another embodiment, the present invention also provides a plasmid capable of expressing the gene product of HIV art/trs in mammalian cells such that infectious HIV particles are not produced, this plasmid including: (1) a DNA fragment comprising an HIV LTR promoter, and (2) an HIV cDNA restriction fragment carrying the art/trs gene but not the ATG start codon of the first coding exon for tat.

BRIEF DESCRIPTION OF THE DRAWINGS

FIG. 1 shows the location of HIV genes and structures of plasmids according to the present invention.

FIG. 1A shows a preferred DNA fragment cloned to generate plasmids expressing gp120. The HIV genome is also shown.

FIG. 2 shows expression of the art/trs and tat gene products. Molecular weight markers are shown and are expressed in kDa.

FIG. 3 shows that gp120 synthesis requires the art/trs and tat proteins.

FIG. 3C represents an 8 hour exposure and FIG. 3D represents a 2 week exposure. Molecular size markers are shown and are expressed in kDa. The arrow indicates the position of gp120.

DETAILED DESCRIPTION OF THE INVENTION

Figure 1B:
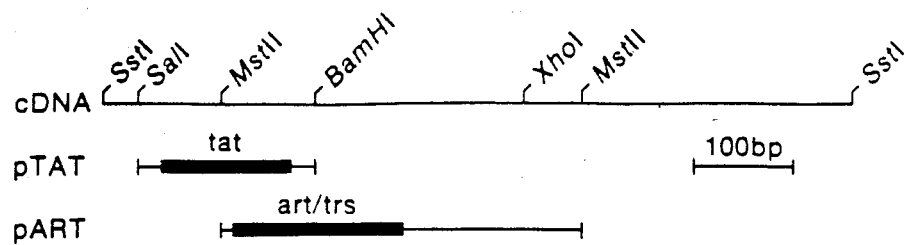
FIG. 1B shows preferred DNA fragments used to construct plasmids expressing tat and art/trs. The DNA fragments are shown beneath the region of the viral cDNA clone pCV-1.

The present assay is based upon the ability of test compounds to inhibit specifically the synthesis of the HIV gp120 envelope protein. The assay is relatively rapid (requiring only several days rather than several weeks) and involves the synthesis of only three viral gene products and therefore is not capable of giving rise to infectious virus particles.

As discussed above, the gp120 protein is a component of the HIV virion and is required for the production of infectious virus. While not desiring to be bound by the following statement, gp120 might also be responsible for a direct cytotoxic effect upon T lymphocytes.

The assay involves the addition of test agents to cells growing in culture that are expressing gp120, tat, and art/trs, from one or more mammalian expression vectors containing the env gene, tat gene and art/trs gene but being incapable of producing infectious virus particles. The ability of the test agents to inhibit expression of gp120 is then measured by a suitable method. A compound that reduces the level of expression of gp120 is a good candidate for an antiviral agent in vivo because of the requirement for gp120 for virus production and the possible direct cytopathic effect of gp120 upon T lymphocytes.

Tat and art/trs are included in the assay because in addition to their role in viral replication, they are also required for gp120 synthesis, as confirmed by the present inventors. Further, tat and art/trs are thought to act early in the cascade of events leading to virion production and therefore are attractive targets, along with gp120, for anti-HIV agents. Also, the inclusion of tat and art/trs provides a greater number of possible targets for inhibition by test agents. Thus, the assay is able to detect agents that interfere with the synthesis or functioning of tat and art/trs as well as those that might interfere with gp120 synthesis at any other level.

All three proteins were chosen for this assay because they are virus-specific and have no known cellular homologs. Thus, the assay detects anti-HIV agents that have minimal toxic effects on normal cells. The specificity for inhibition of the viral proteins or their genes in the assay is guaranteed by the inclusion of an unrelated control gene that produces a protein from a promoter other than that used for production of gp120, tat and art/trs. The amount of unrelated control protein produced in the assay serves as an indicator for non-specific effects of agents on RNA and protein synthesis.

Further the present assay can be performed using a transient expression assay or a stable cell line expressing the env (gp120), tat, art/trs and control protein genes.

Throughout the specification, nucleotide numbers of HIV are referred to. Unless otherwise indicated, the numbers correspond to those using the numbering system of L. Ratner et al., Nature 313, 277 (1985)—expressly incorporated herein by reference.

According to the present invention, one or more mammalian expression vectors carrying the env (gp120), tat, and art/trs genes, all under the control of an HIV LTR promoter and optionally a vector carrying a control protein gene, not under the control of an HIV LTR promoter, all vectors being incapable of producing infectious virus particles, are used to cotransfect cells or to construct a cell line that stably expresses at least the HIV promoted proteins.

As the mammalian expression vector for carrying one or more of the respective genes and the HIV LTR promoter, any vector capable of introduction into mammalian cells can be used as long as the vector carries or can carry the HIV LTR promoter region having a suitable polylinker region containing appropriate restriction sites for cloning the respective genes, if necessary, and suitable RNA processing signals.

For use in a transient expression assay, it is desirable (but not essential) to include the SV40 origin for replication in the vector. When such a vector is introduced into cells which express the SV40 large T antigen (such as Cos-7 cells) the plasmid is capable of replicating to a high copy number thus increasing the expression of the desired genes and, as a consequence, the sensitivity of the assay.

For construction of stable cell lines expressing the desired proteins, it is necessary to have a suitable selectable marker gene on at least one of the transfected vectors in order to isolate those cells which express the transfected DNA. Examples of selectable marker genes include (but are not limited to) the Ecogypt gene, the bacterial neomycin resistance gene, and the dihydrofolate reductase gene (dhfr). Simultaneous multiple selection is possible with different selectable markers on different plasmids, although a single selection may be used with a cotransfection protocol.

Types of vectors that may be used include:
(1) Plasmid-based vectors, for example SV40-derived or Bovine Papilloma Virus (BPV)-derived vectors.
(2) Viral-based vectors, for example:
   (a) Retrovirus vectors, and
   (b) DNA virus vectors including adenovirus and vaccinia, among others.

Additionally, all vectors should contain an origin of replication that enables replication in bacteria such as *E. coli* (for example the origin of replication derived from pBR322) and an antibiotic resistance gene to allow selection for bacteria carrying the vector (for example, the ampicillin resistance gene). These features allow the manipulation and growth of the vectors to be performed using bacteria.

An additional desirable feature of the vector is the elimination of the mRNA splice donor site of HIV at approximately nucleotide numbers +285 to +295, using the numbering system of L. Ratner et al., supra. This feature ensures that the complex regulatory splicing patterns of HIV will not lead to reduced expression of the desired proteins when they are expressed separately. The presence of the splice donor site, natural or synthetic, may be necessary, however, for a construction in which all three genes (env, art/trs, and tat) are on the same vector molecule. For example, the pSNTS plasmid described below contains a synthetic splice donor site. (see "disabled provirus" discussion below). The LTR fragments described later only include sequences up to +80 unless otherwise specified, using the numbering system of L. Ratner et al. supra and therefore do not contain the splice donor site.

Finally, the vector should not contain the DNA sequence ATG between the LTR and the site where the desired fragment is cloned (i.e. in the polylinker). The presence of such an ATG sequence might lead to lower expression of the desired protein due to premature initiation of translation.

Such vectors are well known in the art, and examples of vectors having the above-described characteristics and suitable for use in the present system include pSV2gpt (ATCC #37145, *Science* 209, 1422 (1980)) (This vector already contains suitable RNA processing signals for Ecogpt.); pSV2neo (ATCC #37149 *J. Molec. & Appl. Genetics* 1, 327 (1982)) (This vector already contains suitable RNA processing signals for Neo.); pRSV-gpt (ATCC #37199, *Science* 221, 551 (1983)), pBPV-1(8-2) (ATCC #37110); pZIPNEOSV(X)1 (*Cell* 37, 1053 (1984)) (This vector already contains suitable RNA processing signals.); and pBC12/HIV/t2 (*Cell* 46. 973 (1986)) (This vector already contains an HIV LTR and suitable RNA processing signals.). All references are expressly incorporated herein by reference.

The HIV LTR can be made as follows from methods which are all conventional in the art.

(1) Chemically: Using a DNA synthesizer, the LTR region corresponding to that in the proviral clone λHXB-2, or any proviral clone for which the DNA sequence of the LTR region is known, such as λBH10, λBH5, λBH8 (L. Ratner et al., supra), H9pv.22 (M. Muesing, et al., *Nature* 313, 450 (1985)—expressly incorporated herein by reference.), can be synthesized. A 534 base pair (bp) fragment from base number −454 to number +80 (the numbering system is that of Ratner et al., supra) is sufficient to contain the necessary LTR functions. This sequence (or the analogous one from other HIV isolates) can be constructed initially as smaller fragments which later are joined using DNA ligase to generate the full length fragment. The details of the necessary methods are all conventional in the art.

(2) From newly isolated provirus: The H9/HTLV-III$_B$ cell line (available from the American Type Culture Collection in Rockville, Maryland as ATCC No. CRL 8543 and described in U.S. Pat. No. 4,520,113— expressly incorporated herein by reference) contains multiple copies of HIV proviruses. A provirus containing the LTR (and all viral genes) may be cloned from this cell line using conventional methods as follows.

Total genomic DNA is digested with a restriction enzyme (for example, XbaI) and the resulting genomic restriction fragments are cloned into a bacteriophage λ vector to generate a genomic library. This library is screened by plaque hybridization using a $^{32}$P-labeled synthetic oligonucleotide (assembled on a DNA synthesizer) complementary to a region of the LTR or any other part of the virus based upon the published sequence of Ratner et al., supra. The oligonucleotide can be of any length from about 20 bases on up. Positive clones are isolated and the LTR region subcloned using restriction sites convenient for the particular further manipulations. The HindIII site at nucleotide +80 defines the 3' end of the LTR region: this site is present in all published proviral clones derived from H9/HTLVIII$_B$. The 5' end can be defined by any convenient restriction site in the flanking cellular DNA.

The HIV LTR can also be obtained directly from HTLV-III$_B$ proviral clone λHXB-2 (G. M. Shaw et al., Science 226, 1165 (1984)—expressly incorporated herein by reference) by digestion of λHXB-2 with the restriction enzymes HpaI and HindIII and isolation of the approximately 700 base pair DNA fragment that contains the LTR by gel electrophoresis.

The HIV LTR can also be obtained from any other proviral clone containing the HIV LTR. such as λBH10 and λBH8, by digestion with suitable restriction enzymes and isolation of the DNA fragment that contains the LTR by gel electrophoresis. However, although the HindIII site is common to all known proviral clones from H9/HTLV-III$_B$, the HpaI site is in flanking cellular DNA and therefore would probably not be in other clones. Thus, another site in the flanking DNA needs to be used for these other clones. This site can readily be determined by the skilled artisan.

Suitable RNA processing signals include SV40 RNA processing signals derived from map positions 0–0.19 (polyadenylation signal) and 0.56–0.44 (t-antigen splice signals) of the coding strand of the SV40 genome by cleavage with EcoRI and BclI (polyadenylation) and Sau3A (splice signals) or derived from pRSV-β-globin (available from the American Type Culture Collection in Rockville. Md. and having ATCC deposit number 37200, B. Howard et al., Science 221, 551 (1983)—expressly incorporated herein by reference) by cleavage with BglII and BamHI and isolation of the 847 bp fragment containing both polyadenylation and splice signals.

Other suitable RNA processing signals include the Hepatitis B surface antigen polyadenylation signal (Science, 233, 212 (1980)—expressly incorporated herein by reference) or the natural processing signals from the genes that are being cloned.

Suitable polylinkers are well known to those skilled in the art and can be easily constructed using a DNA synthesizer using the sequences of the desired restriction enzyme recognition sites. Alternatively, a standard polylinker may be obtained by digesting the plasmid pUC19 (Pharmacia cat. #27-4951-01) with EcoRI and HindIII and isolating the polylinker fragment after gel electrophoresis. All methods are conventional in the art.

The fragments and vectors previously described can be assembled into the final expression vector using standard recombinant DNA techniques described in detail in Maniatis, et al., Molecular Cloning—A Laboratory Manual, Cold Spring Harbor Press, 1982—expressly incorporated herein by reference. The precise steps used depend on the exact fragments and vectors used, and are readily determined by those skilled in the art.

The complete vectors containing the HIV LTR, polylinker and appropriate RNA processing signals are constructed from the known vectors and DNA fragments by conventional methods.

The DNA fragment that is cloned into any of the appropriate mammalian expression vectors to generate an expression vector expressing gp120 is a 2768 bp Ava II-XhoI fragment as shown in FIG. 1A obtained from an HIV provirus or cDNA fragment. Any provirus or envelope-containing cDNA derived from the cell line H9/HTLV-III$_B$ is most likely to have these enzyme sites; if these sites are not present in an isolated proviral or cDNA clone, then either another clone can be isolated or other restriction sites outside of the gp120 coding region could be used. Alternative restriction sites are readily determined by the skilled artisan.

In order to make the vector incapable of expressing tat and art/trs, the fragment should not contain the first coding exons of the tat and art/trs genes, which are located at nucleotide numbers 5411–5624 and 5550–5624, respectively, using the numbering system of L. Ratner et al., supra. Also, it is preferred that there be no ATG sequence before the proper ATG start signal for the env protein because this can lead to lower expression.

One preferred DNA fragment for expressing gp120 is one corresponding to the AvaII-XhoI env-containing fragment of λHXB-2 or any proviral clone containing gp120, such as λBH10, λBH3, λBH8, and H9pv.22. FIG. 1A shows the location of the fragment in the HIV genome along with nucleotide numbers which are shown below the AvaII and XhoI sites. (L. Ratner et al., supra).

The DNA fragment that is cloned into any of the appropriate mammalian expression vectors to generate an expression vector expressing tat is an approximately 400 bp fragment containing the tat coding region obtained from: (1) an HIV provirus using tat coding exons from nucleotide numbers 5411 to 5624 and 7955 to 8001 (the numbering system is that of L. Ratner et al., supra); or (2) an HIV cDNA clone containing the tat coding region derived by reverse transcription of either virion RNA or mRNA from H9/HTLV-III$_B$ by conventional procedures (Appropriate restriction sites for excision of tat from cDNA clones are SalI and BamHl as determined by the cDNA sequence published in Arya et al., Science 229, 69 (1985)—expressly incorporated herein by reference); and (3) construction of synthetic DNA encoding tat—a DNA sequence encoding tat can be synthesized using a DNA synthesizer. This sequence can be exactly the same as the published sequence (Ratner et al., supra; Arya et al., supra) (see nucleotide numbers from (1) above) or any DNA sequence derived by reverse translation of the tat protein sequence described in Arya et al., supra. Because of the small size of the tat gene (258 nucleotides) this gene can be easily synthesized by conventional methods.

In order to make the vector capable of expressing only tat and not art/trs, sequences following the Bam HI site (nucleotide number 8052) in the art/trs second coding exon are deleted (J. Sodroski et al., Nature 321, 412 (1986)—expressly incorporated herein by reference).

Again, it is preferable that there be no ATG codons prior to the authentic ATG start codon on the fragments because this can lower expression.

Finally, although the tat gene has two coding exons, only the first one is necessary for the transactivation function of tat. However, the present invention preferably includes both exons because the specific effect of tat on gp120 might be more involved than simply transactivation and thus might require the second exon, although no evidence currently exists to support this hypothesis.

One preferred DNA fragment for expressing tat is one corresponding to the SstI-BamHI fragment containing the entire tat coding region from the viral cDNA clone pCV-1 (I. S. Y. Chen, *Cell* 47, 1 (1986)—expressly incorporated herein by reference)) or from any cDNA clone containing tat, such as H9c171 (Mugsing, et al., *Nature* 313, 450 (1985)—expressly incorporated herein by reference). This DNA fragment is shown in FIG. 1B beneath the region of the viral cDNA clone pCV-1.

The DNA fragment that is cloned into any of the appropriate mammalian expression vectors to generate an expression vector expressing art/trs is an approximately 700 bp fragment obtained from: (1) an HIV provirus using art/trs coding exons from nucleotide numbers 5550 to 5624 and 7955 to 8227 (the numbering system is that of L. Ratner et al., supra); (2) an HIV cDNA clone containing the art/trs coding region derived by reverse transcription of either virion RNA or mRNA from H9/HTLV-III$_B$ by conventional procedures (Appropriate restriction sites for excision of art/trs from cDNA clones are MstII to MstII or MstII to XhoI as determined by the cDNA sequence published in Arya et al., supra); and (3) construction of synthetic DNA encoding art/trs. A DNA sequence encoding art/trs can be synthesized using a DNA synthesizer. The sequence can be exactly the same as the published sequence (Ratner et al., supra; Arya et al., supra) or any DNA sequence derived by reverse translation of the art/trs protein sequence derived from the published DNA sequence. This gene can be easily synthesized because of its small size (387 nucleotides).

In order to make the vector capable of expressing only art/trs and not tat, the ATG start codon for tat must be deleted. It is also preferred that the first 126 bp portion of the first coding exon for tat be deleted.

One preferred DNA fragment for expressing art/trs is the Mst II fragment isolated from pCV-1 or any cDNA clone containing art/trs, such as H9c171. This DNA fragment is shown in FIG. 1B beneath the region of the viral cDNA clone pCV-1.

Each of the gp120 producing, tat producing, and art/trs producing fragments is cloned into the appropriate expression vectors by conventional methods, which may or may not include first subcloning into an appropriate vector such as the well known bacterial vector pUC19.

Figure 1C:
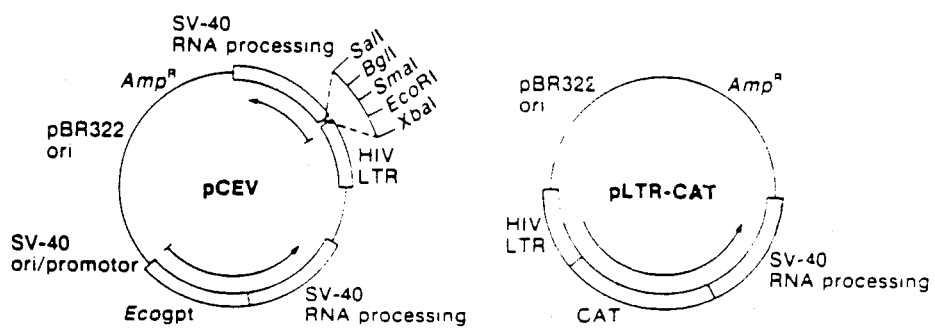
FIG. 1C shows the structures of the expression vectors pCEV and pLTR-CAT. according to the present invention.

One particularly preferred expression vector for carrying the env (gp120), tat and art/trs genes is pCEV, constructed by the present inventors and shown in FIG. 1C.

To construct pCEV, an expression cassette including the HIV LTR obtained as described above, a synthetic polylinker containing the indicated restriction enzyme sites and the SV40 RNA processing signals derived from the well known pRSV-βG are cloned into the EcoRI site of pSV2gpt, available from the American Type Culture Collection in Rockville, Md. and having deposit number 37199. (R. C. Mulligan and P. Berg; *Science* 209, 1442 (1980)—expressly incorporated herein by reference), by conventional methods.

The thus constructed pCEV can be used to prepare plasmids carrying the env (gp120) gene, tat gene, or art/trs gene by inserting the appropriate DNA fragments described above. This is done by conventional methods.

According to the present invention, three preferred plasmids comprising pCEV carrying the env (gp120) gene, tat gene, and art/trs gene designated penv160, ptat and part, respectively, can be constructed as follows.

To construct the plasmid carrying the env (gp120) gene, designated penv160, the Ava II-Xho I env-containing fragment, shown in FIG. 1A, is isolated from λHXB-2 or other proviral clone carrying the env gene such as λBH10, λBH5, λBH8, and H9pv.22 by conventional methods. Because there are internal AvaII sites in the envelope gene, the proviral clone is digested partially with AvaII and completely with XhoI and the appropriate fragment is isolated after agarose gel electrophoresis. The AvaII-XhoI fragment is then blunt-ended by treatment with a Klenow fragment of DNA polymerase I and a mixture of dATP, dCTP, dGTP, and dTTP. The blunt-ended fragment is then subcloned by conventional methods (Maniatis, supra) into the SmaI site of pUC19 for amplification and subsequent ease of excision from pUC19 with appropriate enzymes. The fragment is then excised with restriction endonucleases XbaI and EcoRI. by conventional methods to give a fragment containing the entire AvaII-XhoI envelope region flanked by convenient XbaI and EcoRI sites, supplied by the pUC19 polylinker, for subsequent cloning into pCEV. The XbaI-EcoRI fragment is cloned into the XbaI and EcoRI site (directional cloning) in the polylinker of pCEV by conventional methods. That is, pCEV is digested with both XbaI and EcoRI and the XbaI-EcoRI fragment is ligated in directly to give penv160.

To construct the plasmid carrying the tat gene, designated ptat, the SstI-BamHI fragment shown in FIG. 1B containing the entire tat coding region is isolated from pCV-1 or any cDNA clone containing tat, such as H9c171, by conventional methods. The SstI-Bam HI fragment is then subcloned, by conventional methods, into the SstI and BamHI sites of the pUC19 polylinker for amplification and to supply convenient enzyme sites contributed by the pUC19 polylinkers flanking the insert.

After amplification, a SalI fragment of the Sst I-BamHI subclone in pUC19 (One SalI site is within the SstI-BamHI fragment and the other is in the pUC19 polylinker 3' to the SstI-BamIII fragment. This adds about 6 bp of pUC19 polylinker to the 3' end of the fragment.) is isolated from pUC19 by conventional methods and cloned into the SalI site of the polylinker of pCEV by conventional methods to give ptat.

To construct the plasmid carrying the art/trs gene, designated part, the MstII fragment, shown in FIG. 1B, is isolated from pCV-1 or any cDNA clone containing art/trs, such as H9c171, by conventional methods. The fragment is blunt-ended by filling in the overhanging ends with Klenow fragment of DNA polymerase I and deoxynucleotides, and cloned into the SmaI site of pCEV by conventional methods to give part.

As an alternative to constructing vectors carrying the cloned env, tat and art/trs genes, a "disabled" provirus capable of producing gp120, tat and art/trs but incapable of producing infectious virus particles can be used in the present invention.

Such a "disabled" provirus can be constructed as follows: Starting with a complete provirus derived from H9/HTLV-III$_B$, deletions are made using conventional methods that eliminate all or part of the gag, and/or pol genes. This will disable the provirus without eliminating expression of tat, art/trs or env. The deletions are most easily accomplished by first cloning the provirus into a plasmid vector such as pUC19 or pSV2gpt to allow replication in bacteria. The resulting disabled provirus (in plasmid form) can then be used in the present invention. The disabled provirus is incapable of giving rise to infectious virus because it lacks the ga proteins (components of the virion) and/or the polymerase required for viral replication.

Although such a disabled provirus can be used in the present invention, it is expected to give less than optimal results. Because of the complex regulation of gene expression exhibited by the virus (which is not completely understood) higher levels of the tat, art/trs, and env gene products appear achievable when the genes are removed from their natural setting and expressed independently. One reason for lower expression in proviral form may be that the tat and art/trs proteins are made from the same mRNA molecule; expression of one may inhibit expression of the other thus leading to lower gp120 synthesis and a less sensitive assay.

According to the present invention, a particularly preferred disabled provirus developed by the present inventors is one designated pSNTS, which is capable of producing gp120, tat and art/trs.

This disabled provirus can be constructed as follows: The LTR region from the provirus λHXB-2 or any proviral clone containing the LTR region, such as λBH10 and λBH8 is excised with HpaI and BssHII and isolated after gel electrophoresis by conventional methods. The ends of this fragment are made blunt by treatment with Klenow fragment of DNA polymerase I and deoxynucleotides. EcoRI synthetic linkers (PL Biochemicals) are then ligated to the fragment ends. The resulting fragment is ligated into the EcoRI site of pSV2neo. The EcoRI site now at the 5' end of the LTR fragment is eliminated by partial EcoRI digestion, filling in the ends with Klenow fragment of DNA polymerase I and deoxynucleotides, and religating with T4 DNA ligase. A synthetic oligonucleotide including the viral sequence from the BssHII site (see above) through the viral splice donor site at nucleotide number +289 (numbering system of L. Ratner et al., supra) is inserted in the remaining EcoRI site. This splice donor site may be necessary for adequate expression of the desired viral genes. The synthetic oligonucleotide has an EcoRI site at the 3' end to allow subsequent cloning of an EcoRI fragment.

The proviral clone λHXB-2 or other proviral clone such as λBH10, λBH8, λBH5 and H9pv.22 is digested with XbaI (or other restriction enzyme whose site is present in the 3' flanking DNA but not in the 5' half of the provirus), end-filled with Klenow fragment and deoxynucleotides, and EcoRI synthetic linkers are ligated on, all by conventional methods. The clone is then digested with EcoRI and the approximately 4 kb EcoRI fragment containing env, tat, and art/trs is isolated and cloned into the remaining EcoRI site of the plasmid described above, by conventional methods. The resulting plasmid is essentially a proviral plasmid clone deleted from nucleotide number 293 to number 5323 (the gag and pol regions) (numbering system of L. Ratner et al., supra).

As the control protein, any protein can be used so long as it is unrelated to HIV, can be expressed in mammalian cells, and is easily assayed or quantitated. The protein may be of viral, bacterial, or eukaryotic origin and must be under the control of a suitable promoter, which is not the HIV LTR.

Two types of control proteins are possible: an endogenous cellular protein, or a transfected gene coding for a protein not normally expressed in the cell. A transfected gene is preferred because it would also control for factors relating to transfection (or other introduction method) efficiency, unlike an endogenous gene product.

Examples of suitable control proteins include the bacterial β-galactosidase protein (from a transfected gene) or glycerol phosphate dehydrogenase (an endogenous protein).

One particularly preferred protein is chloramphenicol acetyl transferase (CAT).

As vectors for carrying the control protein, any vector can be used as long as the end product contains a functional promotor and RNA processing signals. These may be supplied by the vector or by the cloned gene. Examples of suitable vectors include (1) pSV2—this supplies the promoter and RNA processing signals and (2) pUC19 —this requires the promoter and RNA processing signals to be supplied by the cloned gene.

A preferred plasmid for expressing the CAT gene is the publically available pSV2-CAT which utilizes the SV40 promoter/enhancer region. (C. M. Gorman et al., *Molecular Cell Biology* 2, 1044 (1982)—expressly incorporated herein by reference).

In order to determine whether the above described vectors express the products of the inserted genes, the following assays can be used.

Expression of the art/trs and tat gene products is assayed by introducing the vector into suitable cells, e.g., Cos-7 cells (available from the American Type Culture Collection. Rockville, Md.—ATCC No. CRL-1651). Hela cells (available from the American Type Culture Collection—ATCC No. CCL2), or any mammalian cells that allow expression of introduced HIV genes, with a suitable amount of the appropriate vector DNA: culturing the cells containing the vectors for a suitable amount of time (e.g. about 48 hours); harvesting the cells; separating the proteins; and analyzing by western blot or other suitable method. For example, measurement of tat activity can also be made indirectly by measuring expression of a suitable indicator protein produced in response to tat production. This is done by introducing into the cells pLTR-CAT DNA (described below) or any other suitable vector expressing a suitable indicator protein by transactivation from an HIV LTR promoter.

When introducing the vectors by transfection, transfection can be carried out by the calcium phosphate coprecipitation method (F. L. Graham, A. J. Van der Eb, *Virology* 5; 456 (1973)—expressly incorporated herein by reference) or other known methods such as DEAE-dextran (Cullen et al., *Nature* 307, 241 (1984)—expressly incorporated herein by reference); electroporation (Potter et al., *PNAS* 81, 7161 (1984)—expressly incorporated herein by reference); or protoplast fusion (Oi et al., *PNAS* 80, 825 (1983)—expressly incorporated herein by reference). The method used depends upon what is most efficient for the cell type used.

One skilled in the art can readily determine specific transfection conditions, for example, by optimizing the amount of tranfected DNA, exposure time of the cells to DNA, and other parameters and culture conditions, for example, cell density, growth medium, etc. The cells are harvested by known methods, e.g., by trypsinization of cells and subsequent concentration by centrifugation.

Methods of introducing vectors by means other than transfection are well known in the art, and include, for example infection of the cells by a viral vector, for example retroviral vectors (C. Rosen, et al., *J. Virol.* 57, 379 (1986) or vaccinia vectors (Chakrabarti et al., *Nature* 320, 535 (1986). Both references are expressly incorporated herein by reference.

The plasmid pLTR-CAT mentioned above for measuring tat activity can be constructed by inserting the HIV LTR, isolated as described above, into the well known plasmid pSVO-CAT at the HindIII site.

The HIV LTR is cloned into pSVO-CAT to produce a plasmid designated pLTR-CAT. shown in FIG. 1C.

Other suitable indicator proteins which can be used in vector form include β-galactosidase from *E. coli*, human interleukin-2, or any protein easily assayed but not endogenous to the cell type used. These same proteins can also be used in viral-based vectors as long as their genes are fused to the HIV LTR, and appropriate RNA processing signals are present.

The western blot analysis is carried out by methods known in the art (Ghrayeb et al. *DNA* 5, 93 (1986)—expressly incorporated herein by reference.) Specifically, proteins are separated by SDS polyacrylamide gel electrophoresis (for example, a 15% polyacrylamide gel is suitable), transferred to nitrocellulose, and allowed to react with appropriate reagents.

To detect art/trs, the material transferred to the nitrocellulose is reacted with a pool of sera from HIV-infected seropositive patients in order to form art/trs—antibody complexes. A radioactively or other appropriately labeled anti-human antibody, such as an $^{125}$I-labeled goat anti-human antibody, is then used to detect immunoreactive proteins according to known methods (J. Ghrayeb, et al., supra).

Expression of art/trs is confirmed by the presence of a 19 kDa immunoreactive protein (See FIG. 2A) which does not react with normal human sera.

Other conventional methods for detecting art/trs include immune precipitation of labeled art/trs protein, reaction with serum directed against purified art/trs proteins, and reaction with polyclonal or monoclonal antibodies specific for art/trs.

Expression of tat is confirmed by measuring the ability of a protein extract to transactivate the HIV LTR fused to an indicator protein gene. A vector carrying HIV LTR fused to a suitable measurable indicator protein gene such as CAT and a vector carrying the tat gene are cointroduced into cells and the level of the indicator protein activity in the protein extract is measured. Increased indicator protein activity over control levels indicates tat expression (J. Sodroski et al., *Science* 227, 171 (1985); J. Sodroski et al., *Science,* 229, 74 (1985) and C. A. Rosen et al., *J. Virology* 57, 379 (1986)—all expressly incorporated herein by reference).

Other suitable methods for detecting tat expression include immune precipitation or western blot using either selected HIV seropositive serum or rabbit antibodies against bacterially synthesized tat (F. D. Veronese et al., *Science* 229, 1402 (1985); A. Aldovini et al., *PNAS* 83, 6672 (1986); Wright et al., *Science* 234, 988 (1986). These methods do not require use of an indicator protein supplied by a separate vector.

In order to assay for gp120 synthesis, a cointroduction protocol according to conventional methods using a combination of env, tat, and art/trs vectors is used.

Suitable cells, as listed above for the art/trs and tat assay, are cointroduced with a suitable amount of vector(s) carrying the env, tat and art/trs genes by suitable methods as described above, cultured for a suitable amount of time (e.g. about 48 hours) and then harvested by known methods. One skilled in the art can readily determine specific introduction and culture conditions.

The proteins can be analyzed by western blot for gp120 production using a pool of HIV-infected patient sera and an appropriately labeled anti-human antibody as described above. Art/trs and tat production can also be analyzed in this assay by the methods described above. Further, if a vector carrying an indicator protein fused to the HIV LTR, such as pLTR-CAT, is included tat production can be measured indirectly by transactivation as described above. A suitable SDS polyacrylamide gel is 12%.

The presence of a band at 120 kDa indicates the presence and thus expression of gp120.

The presence of gp120 can also be measured by incubating an identical western blot with a monoclonal antibody that reacts with purified gp120. Such monoclonal antibodies are commercially available. Reaction conditions are readily determined by the skilled artisan.

Additionally, production of gp120 can be measured by immune precipitation of labeled proteins followed by gel electrophoresis and autoradiography. The details of this method are readily determined by the skilled artisan.

The particular assay used to measure the level of control protein to be used in the assay for anti-HIV agents depends on the particular protein used and is readily determined by the skilled artisan.

For example, if the control protein is CAT. the CAT activity is measured in protein extracts according to Gorman et al. (C. M. Gorman et al., *Molecular Cell Biology* 2, 1044 (1982)—expressly incorporated herein by reference). Specifically, the extract is incubated in the presence of Acetyl CoA and $^{14}$C-chloramphenicol. The products of the reaction $^{14}$C-acetylated chloramphenicol) are separated from the reactants by thin layer chromatography and visualized by autoradiography.

Once it is determined that all vectors are operable, the assay to identify agents that interfere with the life cycle of HIV can be carried out. The assay can be a transient expression assay using cells into which have been introduced vectors expressing gp120, tat, art/trs and, optionally, a vector containing a control protein or the assay can employ a stable cell line expressing env (gp120), tat, art/trs and a control protein.

The transient expression assay will be described first.

In the transient expression assay, vectors capable of expressing HIV gp120, HIV tat, HIV art/trs, all under the control of the HIV LTR promoter, and if an endogenous control protein is not used, a vector containing a control protein, not under the control of the HIV LTR promoter, are cointroduced into mammalian cells. One or more agent(s) suspected of interfering with the life cycle of HIV is added at appropriate times. These times can easily be determined by the skilled artisan, and in general can range from before transfection up until a time before harvesting the cells, as long as the time is sufficient to allow the agent(s) to act. Usually, a range of time points for adding the agent will be employed, for example at intervals of 12 hours. A control cointroduction (no agent added) is also included. The cells are then cultured for a period of time sufficient to allow expression of gp120 in the absence of added agent. In general, this will range from about 12 hours to about 48 hours. After culturing, the cells are harvested and extracts analyzed for production of gp120 relative to the control protein produced. Agents that reduce the relative amount of gp120 produced as compared to the control assay are candidates for therapeutic agents. Any agent which causes a consistent reduction in gp120 is a candidate for further evaluation. The magnitude of the reduction can, but will not necessarily correlate with the effectiveness of the agent in vivo. For this reason, reduction of gp120, regardless of the magnitude, should be followed up with further testing as an anti-HIV agent.

A wide variety of mammalian cell types can be used for the assay. Basically, any mammalian cell types can be used as long as expression of the introduced genes can be achieved. It is preferable to use cells that have been demonstrated to support HIV replication after introduction of provirus (e.g. Cos-7 and Hela). Such cells more closely approximate the in vivo target cells for HIV. H9 (human T cell-derived) cells or other human T cell-derived cell lines may also be used. They very closely approximate in vivo target cells, but are more difficult to grow and transfect.

Suitable examples of cell types which can be used in the present assay include Cos-7. Hela and any mammalian cells that allow expression of introduced HIV genes, as described above for the assays for determining whether the vectors are operable.

Cos-7 cells are especially preferred for plasmid vectors because they are easily transfectable and constitutively produce SV40 T-antigen which allows replication of SV40 ORI-containing plasmids. The benefits of using these cells are readily apparent in view of the desirability of employing vectors that include the SV40 origin of replication for use in the transient assay.

The cells are cultured according to methods known in the art.

Suitable vectors which can be used in the present assay are those described above.

Especially preferred vectors for use in the present assay are the plasmids penv160, ptat, part and pSV2-CAT, all described above.

Introduction of the vectors is accomplished by any suitable method known in the art, such as the calcium coprecipitation method (F. L. Graham and A. J. Van der Eb, supra), DEAE dextran method (Cullen et al., supra), electroporation (Potter et al., supra), protoplast fusion method (Oi et al., supra) or any other introduction method as described above for assaying activity of the vectors.

One skilled in the art can readily determine conditions of introduction according to any of the above methods. However, the following conditions are generally suitable for cotransfection.

Cells are grown to a density of $0.5–2\times10^6$/100 mm dish under culture conditions readily determined by those skilled in the art.

The cells are then cotransfected with the appropriate plasmids in an amount of about 5–10 μg each.

The total amount of DNA is suitably about 20–40 μg (5–10 μg each of 4 plasmids).

Suitable conditions for methods of introduction other than transfection, such as by viral vectors, depend upon the particular vector and cell type used and are readily determined by the skilled artisan.

The amount of agent(s) to be used depends upon the characteristics of the agent and is readily determined by the skilled artisan. If no previous information on the agent is available, a preliminary toxicity test is useful to determine the upper limit. Alternatively, the agent can be tested over a range of amounts of several orders of magnitude. Mixtures of agents can be employed if desired. Synergism among more than one compound is possible, but hard to predict ahead of time. However, it is desirable to test combinations of agents that individually test positive in the assay in order to check for synergistic effects.

The actual cointroduction according to the above method is carried out as follows:

(1) Calcium phosphate coprecipitation (F. L. Graham and A. J. Van der Eb, supra): The appropriate plasmid DNA is added to a calcium chloride solution. This mixture is then added dropwise to a solution of NaCl, HEPES, and Sodium phosphate pH 7.1 and allowed to stand for an appropriate time, e.g. 30 minutes or more. The mixture is then added to the cells in culture medium and incubated under suitable conditions, e.g. overnight at 37° C. in a 5% $CO_2$ atmosphere. The medium is changed if necessary.

(2) DEAE-dextran (Cullen et al., supra): Cells are resuspended in serum-free culture medium containing tris pH 7.3, DEAE-dextran and plasmid DNA, and incubated for an appropriate time at an appropriate temperature, e.g., one hour at 37° C. The cells are washed twice with serum-free medium and plated into dishes.

(3) Electroporation (Potter et al., supra): Cells are washed and resuspended in phosphate-buffered saline (PBS). The plasmid DNA is added, the mixture is placed in an electroporation apparatus and the appropriate current is applied for the appropriate time, e.g. 200 volts for 20 msec. The cells are diluted into culture medium and plated.

(4) Protoplast fusion (Oi. et al., supra): Protoplasts are made from bacteria carrying the plasmids to be transfected using sucrose and lysozyme. The protoplasts are added to cells and fusion occurs in the presence of polyethylene glycol (PEG). The cells are washed and plated.

(5) Infection by viral vectors: As mentioned above, introduction by viral vectors depends upon the particular vector and cell type used. However, as an example, vaccinia vectors may be used to infect sensitive cells at a multiplicity of infection (MOI) of 50 PFU/cell. At least 12 hours after infection the cells are washed 2 times in phosphate-buffered saline (PBS) and analyzed as above. (S. Hu et al., *Nature* 320 537 (1986) expressly incorporated herein by reference).

Once introduction of the vectors is completed, the cells are cultured for a period of time that is at least sufficient to allow expression of gp120.

For most cells, a suitable time period is about 48 hours; three days is generally the maximum amount of time for most cells. A suitable time period ranges from about 12 to 48 hours.

The culture conditions are readily determined by those skilled in the art.

After culturing for a suitable period of time, the cells are harvested by methods known in the art and extracts of total cellular protein are prepared by treatment of cells with trypsin (if the cells are adherent) followed by washing twice with PBS and resuspension of the cells in PBS. For western or dot blot analysis, concentrated lysis buffer is added to bring the cells to 2% SDS, 1.4M $\beta$-mercaptoethanol, 50 mM tris pH 6.8, 10% glycerol, 0.05% bromophenol blue.

The extracts are analyzed by any method which can detect gp120 and any method which can detect the control protein in order to determine non-specific effects on gene expression.

According to the present invention, gp120 can be analyzed by western blot as follows.

The protein extract prepared as described above is run on an SDS polyacrylamide gel in order to separate the total cell proteins. A suitable SDS polyacrylamide gel is approximately 7.5-15%, preferably about 12%. The proteins are then transferred to nitrocellulose and reacted with appropriate antibodies.

A preferred antibody is a monoclonal antibody that recognizes gp120. Such monoclonal antibodies are commercially available, for example #2003-160 from Cellular Products. Inc. Monoclonal antibodies to gp120 do not react significantly with the cellular protein so there is essentially no background signal to reduce sensitivity of the assay in this case.

Proteins reacting with the monoclonal antibody are identified by reacting the monoclonal antibody with a suitable labeled anti-species antibody. For example, if the monoclonal antibody is a mouse monoclonal antibody, the second antibody is an anti-mouse antibody. Suitable labels include radioactive labels such as $^{125}$I, non-radioactive labels such as horseradish peroxidase, alkaline phosphatase or any labels useful for western blots.

The amount of gp120 can then be quantitated by appropriate methods for the probes used. For example, radioactively labeled probes can be quantitated by liquid scintillation counting of the portion of the nitrocellulose filters corresponding to a protein 120 kDa in size or by densotometric scanning of an autoradiograph.

As an alternative to reacting with a monoclonal antibody, the proteins can be reacted with a pool of sera obtained from HIV-infected patients. It is desirable to heat-inactivate any virus in the serum by treatment of the serum at 56° for 1 hour followed by addition of NP-40 (detergent) to 0.5% and incubation at room temperature for 1 hour.

Proteins reacting with the HIV-infected patient sera are then identified by reacting with a suitably labeled anti-human antibody. Suitable anti-human antibodies are commercially available, for example from the Jackson Immunoresearch Laboratories, and include goat anti-human antibodies, or anti-human antibodies from numerous different species. The antibodies can be either polyclonal or monoclonal.

Another possibility for gp120 detection is use of a monospecific polyclonal serum. This can be derived by known methods by injecting a rabbit (for example) with purified gp120, or with fragments of gp120 synthesized in bacteria or made synthetically. The reacted polyclonal antibody is then detected by reacting with a suitably labeled anti-species antibody.

Also for western blot analysis, labeled protein A (which is commercially available) can be used to locate immunoreactive proteins instead of a second antibody (e.g. anti-human or anti-mouse). Protein A can be labeled in any manner as described above for the second antibody. This method however is not as generally applicable as is use of a second antibody because protein A does not react well with all antibody isotypes or species. Protein A detection is described in, for example. S. Chakrabarti et al., *Nature* 330, 535 (1986)—expressly incorporated by reference.

Specific conditions for reacting the western blots with various probes are standard and readily known to those skilled in the art.

As an alternative to detecting gp120 by western blot, a dot blot can be used. This method is similar to a western blot, but rather than separating the total cell proteins on a gel, the total cell protein extracts are simply spotted directly onto nitrocellulose and then treated like a western blot as described above. This method, however, is only suitable if a monoclonal antibody is used so that there is no background and the only signal obtained is due to gp120. This method is quicker and easier to quantitate than the western blot method.

It is also possible (although more cumbersome) to quantitate gp120 by labeling the cells and immune precipitating the HIV proteins using any of the previously mentioned antibodies, followed by gel electrophoresis. If a monoclonal antibody is used and there is essentially no background, then the immune precipitate can be counted by liquid scintillation to quantitate directly without running the proteins on a gel. This procedure might lend itself to automation. Immune precipitation is described in, for example, F. D. Veronese et al., *Science* 229 1402 (1985)—expressly incorporated herein by reference.

Basically, any method of immunological detection can be used for quantitating gp120 according to the present invention. Examples of other methods include Elisa assays and radioimmuno assays, both well known to those skilled in the art.

In order to determine any non-specific effects of the agent on gene expression, the amount of control protein produced in the assay is also determined by methods appropriate to the protein used. For example, if the control protein is CAT, then the method of Gorman et al., described above can be used.

After quantitating the amount of gp120 and control protein in the extracts which contained agent and those which did not contain agent, the relative amount of gp120 in each extract which contained agent and the extract which did not contain agent is determined and these relative amounts compared in order to determine whether the agent decreases the expression of gp120.

Agents that reduce the relative amount of gp120 produced as compared to the relative amount of gp120 produced in the control assay are candidates for therapeutic agents. Any agent which causes a consistent reduction in gp120 is a candidate for further evaluation. However, as already discussed, the magnitude of the reduction can, but does not necessarily correlate with the possible effectiveness of the agent in vivo.

As mentioned above, in addition to the transient assay, the present assay can also be performed using a cell line that stably expresses gp120, tat, art/trs and a control protein. This assay is performed essentially the same as the transient assay, except that the transfections or other means of introducing the vectors are not necessary because the cell line is already stably expressing the env, tat, art/trs, and control protein genes. The agent in this embodiment is simply added to the cells and extracts are analyzed as described above. Mixtures of agents can also be used.

The amount of agent(s) to be used in the stable cell line assay depends upon the characteristics of the agent, just as in the transient assay.

Cells stably expressing g120, tat, art/trs and control protein can be obtained by methods known in the art.

Specifically, plasmids encoding each of the genes are transfected, using any of the above-described methods, into an appropriate cell line (for example Cos-7, Hela) and clones producing the desired proteins are isolated after a selection is applied using appropriate selectable marker genes on the plasmid as described above. One or more selections can be used to select those cells which are expressing transfected DNA. For example, one plasmid encoding gp120 and the neo gene can be co-transfected with the other three plasmids. Clones resistant to G418 can be isolated and screened to identify those that are expressing all of the desired proteins by the methods previously described. Two or more selections can also be used simultaneously. Another possibility is sequential selection using different selectable markers. For example, one plasmid bearing tat and neo can be transfected and tat-producing clones resistant to G418 can be isolated and grown. These cells can then be used to transfect with a plasmid encoding, for example, art/trs and Ecogpt. After selection with mycophenolic acid, clones are isolated that express both art/trs and tat. Other selections may be employed to obtain gp120 and CAT production sequentially. The simplest method is cotransfection of all four plasmids using one selection.

It is also possible to have more than one of the desired genes on one plasmid (for example, pSNTS), and perform one selection.

According to the above method, the present inventors have obtained a Hela cell line stably expressing gp120, tat, and art/trs. This cell line has been designated H-32. H-32 can be derived by transfecting pSNTS (carrying the neo gene) into Hela cells and selecting for G418 resistant cells. H-32 makes gp120 and tat (demonstrated directly) and presumedly makes art/trs since it is required for gp120 synthesis. However, art/trs has not yet been detected from this cell line, probably due to low levels of synthesis. As mentioned before, with the genes in this configuration, gp120 expression is lower than can be achieved with the separately cloned genes. H-32 does not stably express CAT: thus, for expression of a control protein, H-32 can be transfected transiently with a CAT expressing plasmid, or an endogenous cellular protein such as glycerol phosphate dehydrogenase or phosphofructokinase may be used as a control protein instead of CAT.

The invention will now be described by reference to specific examples. However, the examples are not intended to be limiting. Unless otherwise indicated herein, all parts, percents, ratios and the like are by weight.

EXAMPLE 1

Construction of pCEV, penv160, ptat, part, and Disabled Provirus

The construction of these plasmids involves many repetitive procedures. For convenience, some of these procedures will be described first and then referred to later.

(1) Digestion with restriction enzymes: Unless otherwise specified, all digestions were with 1 µg DNA. 5 units of the appropriate enzyme(s) in the buffer specified below. Digestion was for two hours at 37 degrees in a volume of 50 µl.

| Restriction enzyme buffers: | | | | |
|---|---|---|---|---|
|  | AvaII | BamHI | BglI | BglII |
| Tris-HCl pH 7.4 | 6 mM | 6 mM | 10 mM | 10 mM |
| NaCl | 60 mM | 150 mM | 66 mM | 100 mM |
| KCl | — | — | — | — |
| MgCl$_2$ | 10 mM | 6 mM | 10 mM | 10 mM |
| Dithiothreitol | 1 mM | — | 1 mM | 1 mM |
|  | BssHII | EcoRI | HindIII | HpaI |
| Tris-HCl pH 7.4 | 6 mM | 100 mM | 50 mM | 10 mM |
| NaCl | 25 mM | 50 mM | 50 mM | — |
| KCl | — | — | — | 20 mM |
| MgCl$_2$ | 6 mM | 5 mM | 10 mM | 10 mM |
| Dithiothreitol | 1 mM | — | — | 1 mM |
|  | KpnI | MstII | SstI | SalI |
| Tris-HCl pH 7.4 | 6 mM | 6 mM | 6 mM | 6 mM |
| NaCl | 6 mM | 150 mM | — | 150 mM |
| KCl | — | — | — | — |
| MgCl$_2$ | 6 mM | 6 mM | 6 mM | 6 mM |
| Dithiothreitol | 1 mM | 1 mM | 1 mM | 1 mM |
|  | SmaI | PstI | XbaI | XhoI |
| Tris-HCl pH 7.4 | 6 mM | 10 mM | 6 mM | 6 mM (pH 7.9) |
| NaCl | — | 100 mM | 60 mM | 150 mM |
| KCl | 20 mM | — | — | — |
| MgCl$_2$ | 6 mM | 10 mM | 6 mM | 6 mM |
| Dithiothreitol | 1 mM | — | — | — |
| 2-mercaptoethanol | — | — | — | 6 mM |

(2) Filling in the ends of DNA fragments: All end-filling reactions were performed under the following conditions: 5 units of Klenow fragment, 1 mM each of dATP, dCTP, dGTP, and dTTP, 50 mM tris-HCl pH 7.4, 10 mM MgCl$_2$ at room temperature for 30 minutes.

(3) Treatment with Calf intestinal alkaline phosphatase (CIAP): 5 units of CIAP, 50 mM tris-HCl pH 8.5 and DNA in 100 µl vol at 37 degrees for 30 minutes.

(4) All agarose gel electrophoresis was with 1% gels using a buffer of 90 mM tris-borate, 2 mM EDTA. All gels were stained to visualize DNA with 1 µg/ml ethidium bromide.

(5) All transformations used the *E. coli* strain HB101 and were performed by the CaCl$_2$ method. Competent HB101 were prepared by incubating log phase cells in ½ volume 50 mM CaCl$_2$ 10 mM tris-HCl pH 8.0 for 15 minutes on ice. The cells were collected by centrifugation and resuspended in 1/10 volume of the same solution and were then stored frozen for later use. For transformation, the DNA was added to the competent cells and allowed to stand on ice for 30 minutes. The cells were incubated at 42 degrees for 1 minute and 1 ml of L-broth was added. After incubation for 1 hour at 37 degrees, an aliquot of the mixture was plated out on L-plates containing 50 µg/ml ampicillin, and the plates were incubated overnight at 37 degrees.

(6) Ligations were performed in the following buffer: 50 mM tris-HCl pH 7.4, 10 mM MgCl$_2$ 10 mM dithiothreitol, 1 mM spermidine, 1 mM ATP. 1 unit of T4 DNA ligase was used. Ligations were performed overnight at 14 degrees.

(7) Plasmid constructions were verified by performing small scale plasmid preps (minipreps) and digesting the DNA with appropriate restriction enzymes followed by agarose gel electrophoresis. The plasmid preps were performed as follows: Cells from 1 ml of a saturated culture (grown in L-broth plus 50 µg/ml ampicillin) of the bacteria containing the plasmid of interest were resuspended in 100 µl of 50 mM glucose. 10 mM EDTA, 25 mM tris-HCl pH 8.0, 2 mg/ml lysozyme and incubated on ice for 5 minutes. 200 µl of 0.2N NaOH. 1% SDS was added, the solution was mixed, and incubated on ice for 5 minutes. 150 μl of 5M potassium acetate pH 4.8 was added, the solution was mixed and incubated 15 minutes on ice. The mixture was centrifuged in a microfuge for 15 minutes at 4 degrees and the supernatant was extracted once with phenol equilibrated with 10 mM tris-HCl pH 7.4, 1 mM EDTA (TE). The DNA was precipated with 2.5 volumes of 95% ethanol and resuspended in 30 μl TE. 3 μl of this was used for diagnostic restriction enzyme digestion.

Construction of penv, ptat, and part all involves cloning appropriate fragments from HIV into the expression vector pCEV. The construction of pCEV will be described first.

pCEV

10 μg of the HIV proviral clone λHXB-2 were digested with the restriction endonucleases HpaI and XmnI (20 units of each) in 100 μl of HpaI buffer to completion. The 1 kb fragment containing the LTR was isolated after electrophoresis of the mixture on a 1% agarose gel. The ends of the 1 kb fragment were made blunt by treatment with Klenow fragment as described above. The DNA fragment was then ligated into the SmaI site of pUC19 which has been digested with SmaI at 30 degrees C. for one hour followed by treatment with CIAP as described above. The CIAP was inactivated by heating to 65 deg. for 15 min. followed by a phenol extraction and ethanol precipitation. The ligation was performed as described above at a fragment to plasmid molar ratio of 3:1. A portion of the ligation mixture was used to transform the bacterial strain HB101 as described above. Transformants were screened for the presence of the desired plasmid by digesting minipreps with HindIII. One clone containing a plasmid that released a 300 bp fragment after digestion was selected and designated pUCLTR.

pUCLTR was digested with HindIII and the ends were filled in as described above. After heating at 65 deg. for 10 min. the plasmid was digested with EcoRI to completion and the 700 bp fragment released was isolated after electrophoresis on a 1% agarose gel. This 700 bp fragment released was isolated after electrophoresis on a 1% agarose gel. This 700 bp fragment was ligated (as described above) to pUC19 previously cut with EcoRI and SmaI. The HindIII site of this plasmid was destroyed by digestion with HindIII followed by filling in the ends as described above and religating the plasmid to form a circular molecule. This plasmid was designated pUC700. The plasmid pSV2βG (B. Howard et al., *Science* 221. 551 (1983)) was digested with BglII and BamHI and the 847 bp fragment containing the SV40 small t intron and polyadenylation signal was isolated after electrophoresis on a 1% agarose gel. This fragment was ligated to pUC19 which had been digested with BamHI and treated with CIAP as above. After transformation of HB101, a plasmid with the desired orientation of the 847 fragment was identified by digestion with EcoRI and BamHI yielding a fragment of 860 bp. This plasmid was designated pUC860.

The plasmid pUC700 (see above) was digested with HindIII and the ends were filled as described above. After heating at 65 deg. for 15 min. to inactivate Klenow fragment, the plasmid was digested with EcoRI and the 700 bp fragment released was isolated after electrophoresis on a 1% agarose gel. This fragment was ligated into pUC860 which had been previously digested with EcoRI and BamHI. The ligation mixture was used to transform HB101, and plasmid-containing clones were screened by performing mini-plasmid preps followed by digestion with various restriction enzymes. Digestion with EcoRI and HindIII yielded a 1600 bp fragment containing the HIV LTR, XbaI and SalI cloning sites, and the RNA processing signals from SV40. The XbaI and SalI cloning sites were verified by digesting the plasmid with these enzymes in combination with EcoRI or HindIII. Digestion with EcoRI and either XbaI or SalI gave a 700 bp fragment whereas digestion with HindIII and XbaI or SalI yielded a 850 bp fragment. This plasmid was designated pUC1600.

The plasmid pUC1600 was digested with EcoRI and HindIII and the released 1600 fragment was isolated after electrophoresis on a 1% agarose gel. The fragment ends were filled in as described above. This 1600 fragment was ligated into the plasmid pSV2gpt (ATCC #37199) after digesting pSV2gpt with EcoRI and filling in the ends as described above. After transformation of HB101, a clone was selected which had the transcriptional units derived from pSV2gpt and HIV in the same orientation. This was determined by digesting various plasmids with BamHI and BglII and choosing one which released a 1393 bp fragment. This plasmid was digested with XbaI and SalI and a synthetic polylinker containing the enzyme sites XbaI, EcoRI, SmaI, BglII, and SalI was ligated in under conditions described above. The polylinker was synthesized using an Applied Biosystems 38 A DNA synthesizer and has the following sequence:

5'CTAGAGAATTCCGGGAGATCTG 3'

3'TCTTAAGGGCCCTCTAGACAGCT 5'

The two DNA strands of the polylinker were synthesized separately and annealed by heating a mixture of the strands to 60 deg. and letting it cool slowly (approx. 1 hour) to room temperature before ligation.

The resulting plasmid was designated pCEV and has the structure shown in FIG. 1C.

penv160

The EcoRI-PstI fragment (approx. 3800 bp) of λHXB-2 containing the envelope gene was ligated into pUC19 after the plasmid was digested with EcoRI and PstI The resulting plasmid was then digested to completion with XhoI and BglI. 10 μg of DNA from this mixture was partially digested with 10 units of AvaII in 400 μl for 10 min. at 37 degrees. The reaction was stopped by the addition of EDTA to 20 mM and the DNA was precipitated by the addition of 2.5 volumes of 95% ethanol. After centrifugation, the pellet was resuspended in 50 μl 10 mM tris-HCl, 1 mM EDTA pH 7.4 and loaded on a 1% agarose gel. The doublet that migrated at approximately 2800 bp was isolated and the ends were filled in as described above. The mixture was then digested with SalI to reduce the subsequent ligation of the undesired fragment of the doublet. The mixture was then ligated into pUC19 which had been digested with SmaI and treated with CIAP as described above. After transformation, a clone was selected containing a plasmid which released a 2550 bp fragment after digestion with KpnI. This plasmid was designated pUCENV. Plasmid pUCENV was digested with XbaI and EcoRI and the 2550 bp fragment was isolated after electrophoresis on a 1% agarose gel. This fragment was ligated into pCEV which had been digested with XbaI and EcoRI. Transformants were screened and one was chosen that contained a plasmid that released a 2500 bp fragment upon digestion with KpnI. This plasmid was designated penv160.

ptat

The plasmid pCV-1 (Arya et al., Science 229, 69 1985) was digested with SstI, and the 1500 bp fragment was isolated after electrophoresis on a 1% agarose gel. The fragment was ligated to pUC19 which had been digested with SstI and treated with CIAP as described above. After transformation, a clone was chosen whose plasmid released a 1115 fragment upon digestion with BamHI. This plasmid (designated PUCSst) was digested with BamHI and the 3100 bp fragment was isolated after electrophoresis on a 1% agarose gel. This fragment was treated with T4 DNA ligase to recircularize the plasmid (as described above) yielding a plasmid with the pCV-1-derived sequences deleted 3' to the BamHI site. This plasmid was digested with SalI and the 360 bp fragment containing the tat gene was isolated after electrophoresis on a 1% agarose gel. This fragment was ligated to pCEV which had been previously digested with SalI and treated with CIAP as described above. After transformation, one clone was selected which contained a plasmid with the tat gene in the correct orientation as determined by the release of 1224, 1547, and 231 bp fragments after digestion with AvaII. This plasmid was designated ptat.

part

The plasmid pUCSst (see above) was digested with MstII and the 720 bp fragment released was isolated after electrophoresis on a 1% agarose gel. The ends of this fragment were filled as desribed previously. The fragment was then ligated to pCEV which had been previously digested with SmaI and treated with CIAP. After transformation, a clone was chosen whose resident plasmid released a 1639 bp fragment upon digestion with BamHI. This plasmid was designated part.

pSNTS

The plasmid pUCLTR (see above) was digested with BssHII and the ends were filled in as described above. 1 μg EcoRI synthetic phosphorylated linkers (PL biochemicals) were ligated to the blunt ends using T4 DNA ligase under the standard ligation conditions. The ligase was inactivated by heating at 65 degrees for 15 minutes and the mixture was digested with 50 units of EcoRI overnight. The mixture was subjected to electrophoresis on a 1% agarose gel and the 900 bp fragment (now with two EcoRI ends) was isolated and cloned into pSV2neo (ATCC #37149) which had been previously digested with EcoRI and treated with CIAP. A clone was chosen whose plasmid released a 1450 bp fragment after digestion with BamHI and HindIII (in BamHI buffer). To destroy the EcoRI site 5' to the LTR, this plasmid was partially digested with EcoRI under the following conditions: 10 μg of DNA, 2 units of EcoRI, 15 minutes at 37 degrees in a volume of 100 μl. After inactivation of the enzyme by extraction with an equal volume of phenol (equilibrated with 10 mM tris-HCl pH 7.4, 1 mM EDTA), the ends of the DNA molecules were filled in as described above. The DNA was then precipitated with 2.5 volumes of 95% ethanol and resuspended in 10 μl ligase buffer. 1 unit of T4 DNA ligase was added and the mixture was incubated overnight at 14 degrees. After transformation of HB101, a clone was selected whose plasmid released a 1650 fragment after digestion with BamHI and EcoRI. This plasmid was designated pSNL.

An oligonucleotide was synthesized (as previously described) containing the splice donor site from HIV at approximately nucleotide #285–295. The sequence is as follows:

```
5'AATTAAGAGGCGAGGGGCGG-
   CGACTGGTGAGTACCCGGG 3'

3'TTCTCCGCTCCCCGCCGCTGACCACT-
   CATGGGCCCTTAA 5'
```

This oligonucleotide was ligated into pSNL which had been previously digested with EcoRI and treated with CIAP. After transformation of HB101 a clone was chosen whose plasmid had acquired the SmaI site from the oligonucleotide. This plasmid was designated pSNLS. The proviral clone λHXB-2 was digested with XbaI and the ends were filled in as described above. Synthetic EcoRI linkers were ligated to the DNA ends (see procedure above) and the DNA was digested with EcoRI. The approximately 4 kb EcoRI fragment was isolated after agarose gel electrophoresis and ligated into pSNLS which had previously been digested with EcoRI and treated with CIAP. After transformation of HB101, a clone was selected whose plasmid released a 1600 bp fragment (among others) after digestion with BglII. This plasmid was designated pSNTS.

EXAMPLE 2

Expression of art/trs and CAT Gene Products

Cos-7 cells were plated at a density of $2 \times 10^6$ cells/plate and transfected 24 hours later with 10 μg of the appropriate plasmid DNA (as indicated in FIG. 2) by the calcium phosphate coprecipitation method (F. L. Graham and A. J. Van der Eb, Virology 52, 456 (1973)). 5 μg pLTR-CAT was included to enable measurement of tat activity. pUC19 plasmid DNA was added to keep the total amount of DNA at 35 μg in all cases. Cells were incubated for 48 hours at 37° C. in a 5% $CO_2$ atmosphere. After 48 hours incubation, the cells were harvested by the addition of 1.5 mls trypsin (0.05%)-EDTA (1 mM) and incubated at 37 degrees for approximatley 15 minutes. The cells were collected by centrifugation at $1500 \times g$, washed once in Phosphate-buffered saline (PBS), and resuspended in 100 μl of PBS. 5 μl of the cell suspension was removed for subsequent assay for CAT activity. The remaining cell suspension was diluted at 250 μl with PBS and $5 \times$ SDS lysis buffer was added to bring the mixture to $1 \times$. $1 \times$ SDS lysis buffer is 2% SDS, 1.4M 2-mercaptoethanol, 50 mM tris-HCl pH 6.8, 0.05% bromophenol blue, and 10% glycerol. The samples were sonicated (approx. 1 min.) to reduce viscosity if necessary, and boiled for 3 minutes before loading on the gel. Proteins were separated on a 15% SDS polyacrylamide gel (using the gel system of U. K. Laemmli. Nature 227, 680 (1970).), transferred to nitrocellulose electrophoretically using a BIORAD transblot apparatus using the buffer recommended by the manufacturer, i.e. 20% aqueous methanol containing 0.016M tris base and 0.13M glycine, and allowed to react with blocking buffer (5% non-fat dry milk, 0.1% sodium azide, 0.1% antifoam, all in PBS) for 30 minutes (J. Ghrayeb, et al., DNA 5, 93 (1983)) at 37° followed by blocking buffer containing 5% goat serum at room temperature for 30 minutes or more. A pool of sera from HIV-infected patients was added at a 1:100 dilution. An $^{125}$I-labeled goat anti-human second antibody obtained by labeling unlabeled antibody from Jackson Immunoresearch Laboratories by known methods was then used to detect immunoreactive proteins according to the method of Ghrayeb et al., DNA 5, 93 (1986).

Figure 2B:
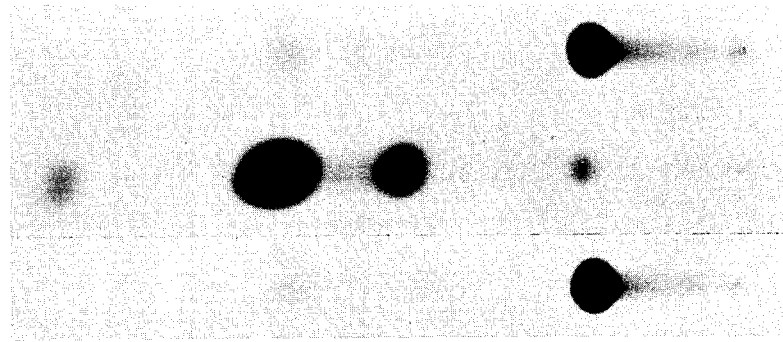
FIG. 2B is an autoradiograph of chloramphenicol acetyltransferase (CAT) assays performed on the same cell extracts as in FIG. 2A and shows that tat protein is synthesized when Cos-7 cells are transfected with ptat.
Figure 2A:
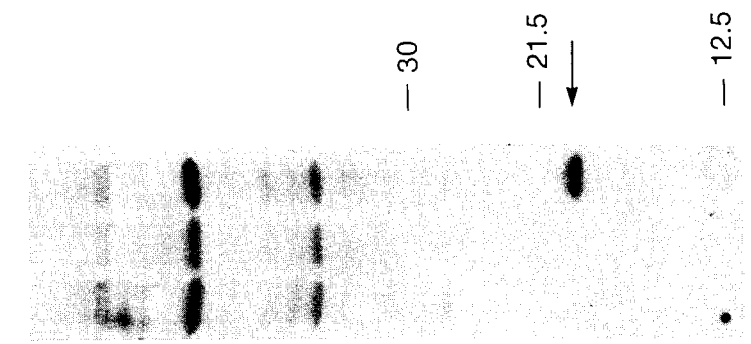
FIG. 2A is an autoradiograph of HIV-immunoreactive proteins present in a western blot of total cell proteins from mock-transfected cells, ptat-transfected cells and part-transfected cells, respectively. The arrow indicates the 19 kDa art/trs gene product.

The results are shown in FIG. 2A. The positions of the molecular size markers are shown (size expressed in kDa), and the arrow indicates the position of the 19 kDa immunoreactive protein which is the product of the art/trs gene of HIV.

The 19 kDa is apparent only in part transfected cells and not in mock transfected cells or in cells transfected with ptat, the 19 kDA protein did not react with normal human sera.

The calculated molecular weight of art/trs based upon the deduced amino acid sequence is approximately 13.6 kDa. The higher apparent molecular weight that is observed in the present invention may be due to the high proline content of the protein which is thought to decrease the mobility of certain proteins in SDS acrylamide gels (W. C. Goh et al., J. Virology 59, 181 (1986) and K. Nagashima et al., J. Virology 60, 394 (1986)). These results demonstrate that the art/trs gene can be expressed at high levels as a 19 kDa protein that is immunoreactive with sera from HIV seropositive patients.

Extracts from the same experiment were assayed for CAT activity as described in C. M. Gorman et al., (C. M. Gorman et al., Molecular Cell Biology, 2, 1044 (1982)). The results are shown in FIG. 2B.

FIG. 2B shows that transactivation of the HIV LTR occurs only when ptat is transfected, indicating that ptat expresses that tat protein.

FIG. 2 also confirms that only the expected viral gene products are made from the tat and art/trs plasmids. When part is cotransfected with pLTR-CAT, there is no transactivation indicating that no detectable tat is present (FIG. 2B). Similarly, transfection of Cos-7 cells with ptat does not produce the 19 kDa immunoreactive art/trs protein (FIG. 2A).

Figure 3B:
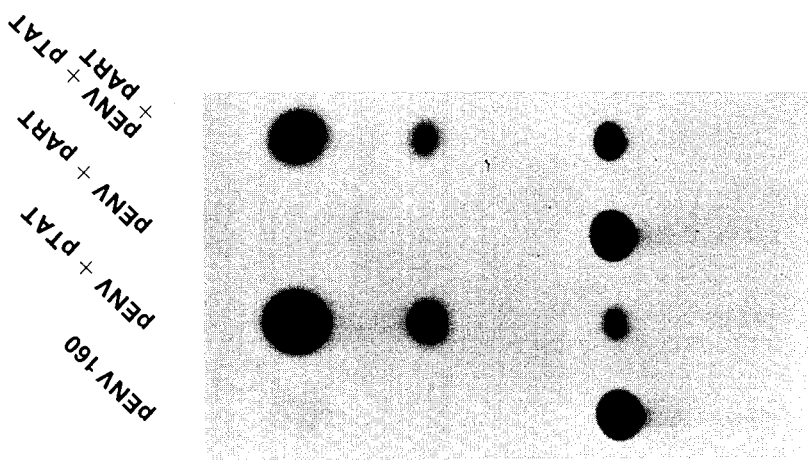
FIG. 3B is an autoradiograph of CAT assays performed on the same cell extracts as in FIG. 3A and shows that tat protein is expressed when cells are transfected with tat.

EXAMPLE 3 gp 120 Synthesis gp120 synthesis requires the art/trs and tat gene products. Thus Cos-7 cells were transfected as described in Example 2 with 10 μg of each of the plasmids indicated in FIG. 3. 5 μg of pLTR-CAT was included in each transfection to enable measurement of tat activity, and the total amount of DNA was held constant at 35 μg by the addition of pUC19 DNA. The cells were incubated for 48 hours as described in Example 2 and harvested as described in Example 2. Then extracts of total cellular protein were prepared as described in Example 2. The extracts were analyzed for gp120, art/trs, and tat activity as follows.

Total cell proteins were separated on a 12% SDS polyacrylamide gel using the gel system of Laemmli, supra, tranferred to nitrocellulose as described in Example 2, and reacted with a pool of HIV-infected patient sera as described in Example 2. An $^{125}$I-labeled goat anti-human second antibody as described in Example 2 was used to detect immunoreactive proteins.

Figure 3A:
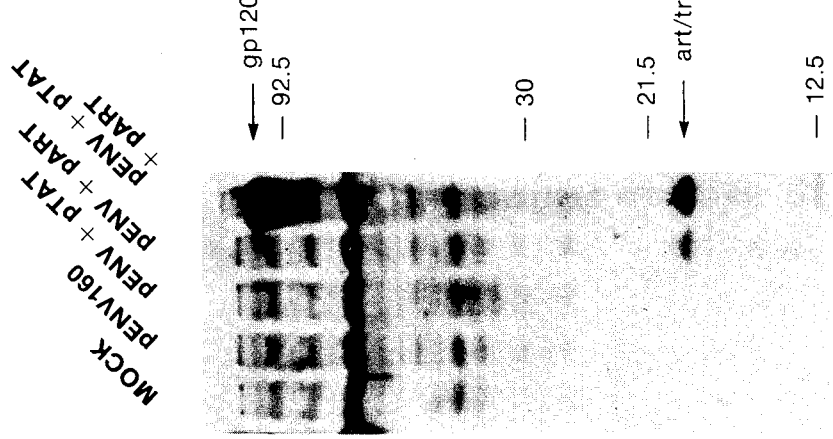
FIG. 3A is an autoradiograph of proteins immunoreactive with serum from HIV seropositive patients present in a western blot of total cell, proteins from mock transfected cells. penv160-transfected cells, penv+ptat-transfected cells, penv+part-transfected cells, and penv+ptat+part-transfected cells. Molecular size markers are shown and are expressed in kDa. The arrow indicates the positions of the art/trs and gp120 proteins.
Figures 3C, 3D:
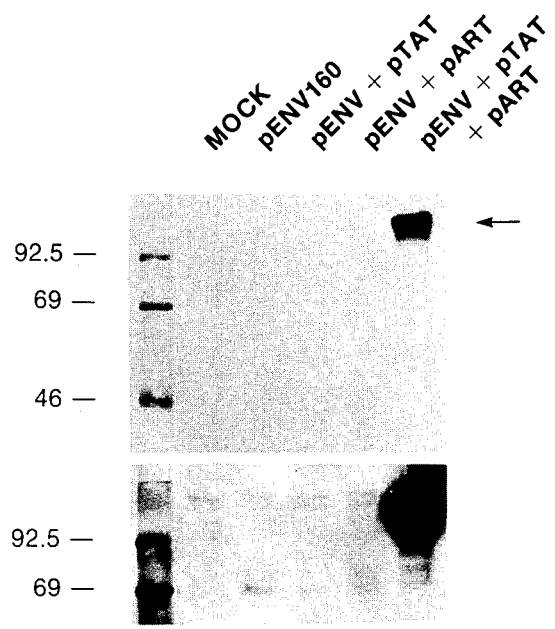
FIGS. 3C and 3D are autoradiographs of proteins that react with a monoclonal antibody to purified gp120 present in the same western blot described in FIG. 3A.

The results are shown in FIG. 3A. The positions of the molecular size markers are shown (size expressed in kDa). and the positions of the art/trs and gp120 proteins are marked with arrows.

As described above, pen160 which contains the entire coding region of the envelope gene fused to the HIV LTR was used to express gp120. The gp160 precursor protein and the gp41 transmembrane protein are also encoded by penv160: the methods of gp120 analysis however, did not reproducibly detect these proteins. Also, this plasmid does not contain the first coding exons of the tat and art/trs genes, and is therefore incapable of expressing these proteins In order to measure tat activity. CAT assays were performed on the same extracts according to the method described in Example 2.

FIG. 3A shows that when pen160 was transfected into cos-7 cells, no gp120 was detected. When pen160 was co-transfected with ptat still no gp120 was seen, even though functional tat protein was present (FIG. 3B), indicating that tat alone is incapable of transacting gp120 synthesis. When part was co-transfected with penv160, art/trs protein was expressed but again no gp120 was detected (FIG. 3A). In contrast, when pen160 was co-transfected with both ptat and ptat, there was a strong band corresponding to gp120. Note that the amount of art/trs is increased in the presence of tat, presumably due to tat-mediated transactivation of the LTR of part.

To confirm the identify of the gp120 band and to detect possible low levels of gp120, an identical western blot was incubated with a murine monoclonal antibody that reacts with purified gp120. This result (FIG. 3C) confirms the pattern of gp120 expression observed in FIG. 3A. In addition, a long exposure of the same blot (FIG. 3D) reveals no gp120 in the absence of art/trs or tat allowing the conclusion that both tat and art/trs are absolutely required for gp120 synthesis using the HIV LTR as the promoter.

The increase in gp120 is not simply due to increased transactivation of the LTR with art/trs present because the transactivation levels measured by CAT assay are no higher with ptat plus part than with ptat alone (FIG. 3B).

While the invention has been described in detail and with reference to specific embodiments thereof, it will be apparent to one skilled in the art that various changes and modifications can be made therein without departing from the spirit and scope thereof.

We claim:

1. A virus-free assay to identify agents that interfere with the life cycle of HIV which comprises:
   (1) expressing in mammalian cells, in the presence or absence of one or more of said agents,
      (a) HIV gp120, the gene product of HIV tat, and the gene product of HIV art/trs, all under the control of an HIV LTR promoter, and
      (b) a control protein, not under the control of said HIV LTR promoter,
   such that infectious HIV particles are not produced;
   (2) quantitating the amount of the gp120 produced relative to the amount of the protein produced; and
   (3) comparing the relative amount of the gp120 produced in the presence of said one or more agents to the relative amount of the gp120 produced in the absence of said one or more agents.

2. The assay of claim 1, wherein said HIV gp120, the gene product of HIV tat, and the gene product of HIV art/trs are expressed transiently by introducing into said cells vectors carrying genes for said HIV gp120, the gene product of HIV tat, and the gene product of HIV art/trs.

3. The assay of claim 1, wherein said HIV gp120, the gene product of HIV tat, the gene product of HIV art/trs and the control protein are expressed transiently by introducing into said cells vectors carrying for said HIV gp120 the gene product of HIV tat, the gene product of HIV art/trs and the control protein.

4. The assay of claim 1, wherein said HIV gp120, the gene product of HIV tat, and the gene product of HIV art/trs are stably expressed by said cell.

5. The assay of claim 2, wherein said vectors carrying genes for said HIV gp120, the gene product of HIV tat, and the gene product of HIV art/trs are penv160, ptat, and part, respectively.

6. The assay of claim 3, wherein said vectors carrying genes for said HIV gp120, the gene product of HIV tat, the gene product of HIV art/trs, and the control protein are penv160, ptat, part, and pSV2-CAT, respectively.

7. A plasmid capable of expressing the gene product of HIV art/trs in mammalian cells such that infectious HIV particles are not produced, which comprises: (1) a DNA fragment comprising an HIV LTR promoter, and (2) an HIV cDNA restriction fragment carrying the art/trs gene but not the ATG start codon of the first coding exon for tat.

8. The plasmid of claim 7, wherein the HIV cDNA restriction fragment carrying the art/trs gene but not the ATG start codon further lacks the initial 126 base pairs of the first coding exon for tat.

9. The plasmid of claim 7, wherein the HIV cDNA restriction fragment is the Mst II fragment isolated from a cDNA clone containing art/trs.

10. The plasmid of claim 7, designated part.

* * * * *